(12) United States Patent
Schann et al.

(10) Patent No.: US 7,374,929 B2
(45) Date of Patent: May 20, 2008

(54) DEVICE FOR MICROBIOLOGICAL EXAMINATION OF A SAMPLE OF LIQUID UNDER PRESSURE

(75) Inventors: Christian Schann, Oberhausbergen (FR); Gérard Muller, Urmatt (FR); Frédéric Reynes, Molsheim (FR); Christian Clauss, Obernai (FR)

(73) Assignee: Millipore Corporation, Billerica, MA (US)

( * ) Notice: Subject to any disclaimer, the term of this patent is extended or adjusted under 35 U.S.C. 154(b) by 683 days.

(21) Appl. No.: 10/491,059

(22) PCT Filed: Oct. 9, 2002

(86) PCT No.: PCT/EP02/11336
§ 371 (c)(1),
(2), (4) Date: Mar. 29, 2004

(87) PCT Pub. No.: WO03/033641
PCT Pub. Date: Apr. 24, 2003

(65) Prior Publication Data
US 2004/0241785 A1 Dec. 2, 2004

(30) Foreign Application Priority Data
Oct. 12, 2001 (FR) .................................. 01 13185

(51) Int. Cl.
*C12M 1/12* (2006.01)
(52) U.S. Cl. ............... 435/308.1; 435/297.2; 435/297.5; 422/101; 210/406; 210/445; 210/455; 210/321.84

(58) Field of Classification Search ............. 435/297.2, 435/297.5, 308.1; 422/101; 210/445
See application file for complete search history.

(56) References Cited

U.S. PATENT DOCUMENTS

| 3,275,528 | A |   | 9/1966 | Ainis ........................ 195/104 |
| 3,308,558 | A |   | 3/1967 | Orlando ...................... 34/218 |
| 4,678,576 | A | * | 7/1987 | Leoncavallo ........... 210/321.87 |

FOREIGN PATENT DOCUMENTS

| WO |   | 01/48142 |   | 7/2001 |
| WO | WO 200148141 A1 | * | 7/2001 |

* cited by examiner

*Primary Examiner*—William H Beisner
(74) *Attorney, Agent, or Firm*—Nields & Lemack

(57) ABSTRACT

This concerns a device whose filtering membrane (4) is gripped annularly at the periphery between an annular transverse wall (32) forming part of a drainage body and an axially oriented cylindrical wall (9) of an intake body, which lateral wall has an elastomer seal (13) which forms the edge thereof and by means of which this wall comes into contact with the membrane (4), this device being provided with a second seal (55) which has an arched profile, the external annular end (61) of which bears against said annular transverse wall (32) radially beyond said membrane (4), and the internal end (57) of which is connected to said seal (13) on the lateral wall (9) of said reservoir (5), hereinafter referred to as the first seal.

15 Claims, 3 Drawing Sheets

DEVICE FOR MICROBIOLOGICAL EXAMINATION OF A SAMPLE OF LIQUID UNDER PRESSURE

The invention relates to devices for the microbiological examination of a liquid sample under pressure.

Through French patent applications 2 802 942 and 2 802 943, such a device which has an intake body, a filtering membrane and a drainage body is already known. The intake body has a reservoir, in one wall of which a liquid inlet orifice is provided, the membrane closing off this reservoir, the drainage body being designed to support the membrane on the opposite side to the reservoir and being provided with a liquid outlet orifice, the intake body and the drainage body locking on each other by means of snapping on in the axial direction, the membrane being gripped annularly at the periphery between an annular transverse wall of the drainage body situated around means with which this body is provided for supporting the membrane and the lateral wall of the reservoir of the intake body, which lateral wall has an elastomer joint which forms the edge and through which this wall comes into contact with the membrane, this joint, although it is present on only one of the faces of the membrane, makes it possible to obtain a seal on the two faces of the latter, because of the simple fact that the above mentioned two walls grip the membrane.

The taking of a sample to be examined is effected by connecting the inlet orifice of the reservoir of the intake body to a pressurised liquid source, so that the reservoir fills with this liquid, which can leave it only through the filtering membrane, this liquid being recovered on the other side of the membrane by the drainage body and discharged out of the latter through the outlet orifice.

By virtue of the seal procured by the gripping of the membrane, all the liquid which has passed through the membrane escapes from the drainage body through the outlet orifice in the latter, so that, by collecting the liquid discharged through the outlet orifice in a graduated receptacle, the volume of the sample of liquid which is passed through the membrane is known with precision.

This is then put to incubate in contact with a nutrient medium under predetermined conditions, notably of temperature and duration, so that the micro-organisms retained by the membrane during the sampling grow, the result of the microbiological examination being supplied by the identification and numbering of the colonies of micro-organisms present on the membrane at the end of the incubation period.

The invention relates to a device of the same type, but with improved performance with regard to reliability and convenience of use.

It proposes for this purpose a device for the microbiological examination of a sample of liquid under pressure, having an intake body, a filtering membrane and a drainage body, the said intake body having a reservoir, in one wall of which a liquid inlet orifice is provided, said membrane closing off said reservoir, said drainage body having means of supporting said membrane opposite to said reservoir and a liquid outlet orifice, said inlet body and said drainage body having mutual locking means, said membrane being gripped annularly at the periphery between an annular transverse wall of the drainage body situated around said membrane support means and the lateral wall of said reservoir of the intake body, which lateral wall has an elastomer joint which forms the edge and through which this wall comes into contact with said membrane; characterised in that said device is provided with a second joint which has an arched profile, the external annular end of which bears against said annular transverse wall radially beyond said membrane, and the internal annular end of which is connected to said joint which the lateral wall of said reservoir has, hereinafter referred to as the first joint.

The first joint and the second joint form together a double-joint sealing ring, the first and second joints being connected to each other at the internal annular end of the second joint.

The portion of the membrane situated around the first joint is isolated from the outside by virtue of the second joint, the arched profile of the latter making it possible to create a closed chamber opposite this portion.

The second joint thus procures protection of the annular portion of the membrane situated further to the outside than the first joint, vis-à-vis contamination by micro-organisms related to the environment.

Thus the risk of falsifying the result of the analysis through the presence of micro-organisms not coming from the liquid sample to be examined is avoided.

In addition, the existing chamber, opposite the outermost portion of the membrane, by virtue of the second joint, can collect, during an operation of sampling a liquid under pressure, any discharge of this liquid due to internal leaks at the membrane at the point where it is gripped, these leaks originating in the lateral capillary attraction of the membrane. The escape of this discharge from the device is thus prevented in the majority of cases, which improves its convenience of use.

According to characteristics which are preferred both for the convenience of use and for the quality of the results obtained, said second joint has:
  a first cylindrical wall, a first end of which forms said internal end connected to said first joint and whose internal surface is opposite a rigid part of said lateral wall of said reservoir;
  a frustoconical wall, the internal end of which is connected to said second end of the first cylindrical wall; and
  a second cylindrical wall, a first end of which is connected to said frustoconical wall and the second end of which forms said external annular end of the second joint.

Preferably:
  said intake body has a frustoconical wall, the small-diameter end of which is connected to said lateral wall of the reservoir; in that the internal surface of the first cylindrical wall of the second joint has the same conformation as the external surface of said lateral wall between said first joint and said frustoconical wall of the intake body; and in that the external surface of said frustoconical wall of the second joint has the same inclination as the internal surface of the frustoconical wall of the intake body; and possibly
  the small diameter of the external surface of the frustoconical wall of the second joint corresponds to the small diameter of the internal surface of the frustoconical wall of the inlet body whilst the large diameter of the external surface of the frustoconical wall of the second joint is slightly smaller than the large diameter of the internal surface of the frustoconical wall of the intake body; and/or possibly
  said frustoconical wall of the intake body forms part of a skirt carrying said locking means with which the intake body is provided; and/or
  said second cylindrical wall has, on the inside, as from said external annular end, a bevel; and possibly said second end of the second cylindrical wall of the second joint is substantially at the same level as said internal annular end of said second joint.

According to other preferred characteristics, for the same reasons:

a groove is provided at the end of a rigid part of said lateral wall when said first joint has a T-shaped profile whose longitudinal leg forms a rib inserted in said groove and whose transverse leg forms a protrusion in contact with the membrane; and possibly there exists a bevel between the rib and the protrusion on the external side, whilst on the internal side the rib and protrusion are connected by a straight surface.

According to other preferred characteristics, for the same reasons, said first joint and said second joint are formed by a sealing ring formed in a single piece.

According to yet other preferred characteristics, in order to enable the first joint and/or the sealing ring to co-exist as well as possible with the membrane, it is through a screen ring that said first joint comes into contact with said membrane.

The screen character of this ring prevents the migration to the membrane of the constituents of the elastomer material from which the sealing ring and/or the first joint are made, which avoids interfering with the correct growth of the micro-organisms on the membrane when the latter, subsequent to the sampling operation, is put to incubate.

According to preferred characteristics, because of the convenience of use and the quality of the results obtained:

said screen ring is made from a very thin film of polypropylene; and/or the screen ring is held on said first joint; and/or the internal diameter of said screen ring corresponds to the internal diameter of a cushion on said first joint; and/or the external diameter of said screen ring corresponds to the internal diameter of a cylindrical wall situated on the external side of said second joint.

It should be noted that the use of the sealing ring which has just been disclosed is also advantageous when there is no second joint.

The explanation of the invention will now be continued with the description of an example embodiment, given below as a non-limitative illustration, with reference to the accompanying drawings. In these:

Figure 1:
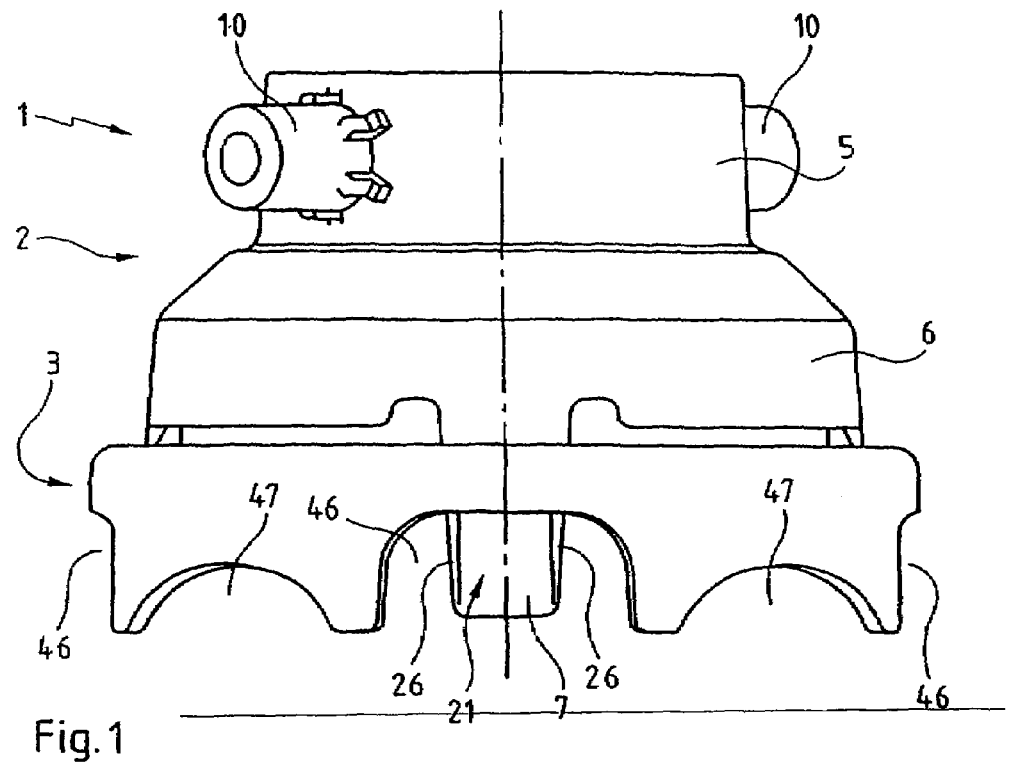
FIG. 1 is an elevational view of a device in accordance with the invention.
Figure 2:
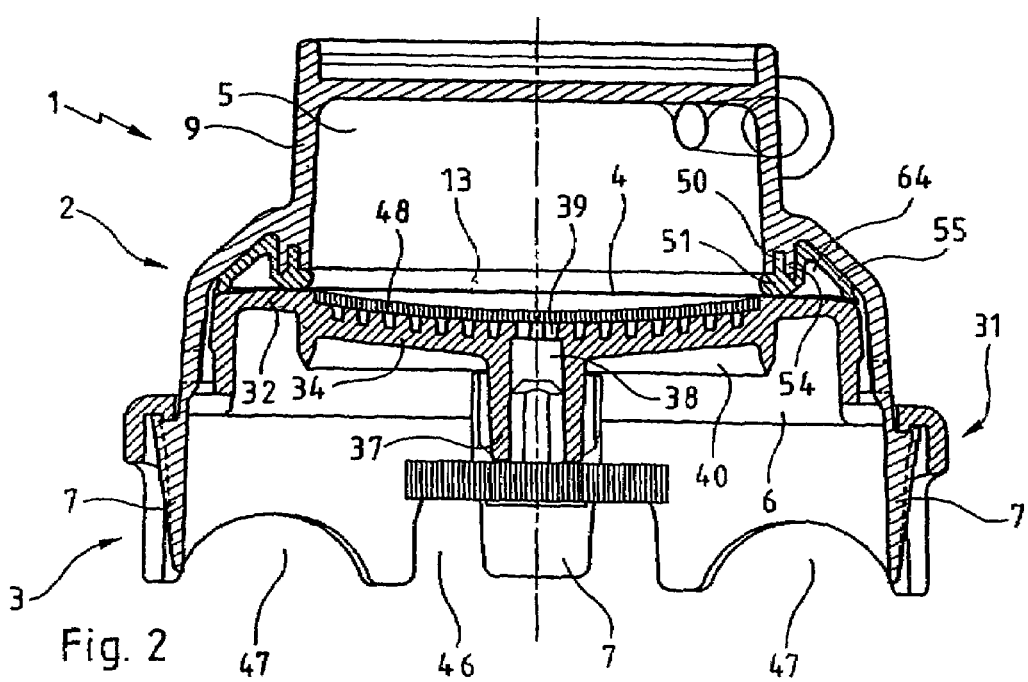
FIG. 2 is a sectional elevational view of this device.

The device 1 for microbiological examination of a sample of liquid under pressure shown in the drawings, and notably in FIGS. 1 and 2, has in general terms a symmetry of revolution around a central axis. It has an intake body 2, a drainage body 3 and a filtering membrane 4.

The intake body 2 has a reservoir 5, a skirt 6 which is connected externally to the reservoir 5 and four latching tabs 7 which extend projecting from the skirt 6, in an axial direction.

The reservoir 5 has an end wall 8 and a lateral wall 9.

Two diametrically opposite pipes 10 extend projecting outward from the lateral wall 9, above the skirt 6, each of these pipes constituting a female Luer connector adapted to receive internally, in order to sample a liquid under pressure, a male Luer connector, the passage internal to each pipe 10 being continued by an aperture 11 made in the wall 9, this aperture being in immediate proximity to the end wall 8.

The lateral wall 9 finishes at the end opposite the end wall 8 in an edge forming part of a seal 13, a groove 14 being made to that effect in the rigid part of the wall 9, as will be explained in more detail subsequently with the help of FIGS. 2, 3, 6 and 7.

The skirt 6 is connected to the reservoir 5 by the outside of the lateral wall 9, at a level situated between the groove 14 and the pipes 10, the skirt 6 having a truncated-cone shaped wall 15 and a cylindrical wall 16, the skirt 6 being connected to the wall 9 by the small-diameter end of the wall 15 while the connection between the walls 15 and 16 is made by the large-diameter end of the wall 15, the connection between the walls 15 and 16 being situated approximately at the level of the edge of the wall 9.

Each of the latching tabs 7 has a general outline in the form of a trapezium symmetrical with respect to the axial direction, the side forming the free end 18 of the tab 7 being parallel to the one by which this tab is connected to the skirt 6, and more precisely to the edge of the wall 16, the tab 7 narrowing steadily between its connection to the skirt 6 and its free end.

On either side of each tab 7, a notch 17 is made in the wall 16, over a certain distance from the edge thereof.

Each tab 7 has, from its free end 18, an internal surface 19 which is straight, that is to say parallel to the axial direction, as far as a dihedral 20 from which the surface 19 is inclined inward and towards the wall 16.

As for the external surface 21 of each tab 16, this is inclined outward and towards the wall 16, the surface 21 extending between the surface 18 and a transversely oriented surface 22 which connects the surface 21 and a groove 23 situated between an external shoulder 24 whose surface 22 constitutes the edge and a surface 25 offset inward with respect to the surface 21, the surface 25 being in the continuation of the external surface of the wall 16.

It should be noted that the portion of each tab 7 situated between the bottom of the groove 23 and the edge of the wall 16 has a thickness which is a minimum at the level of the dihedral 20.

Consequently, it is in the region of the dihedral 20 that the tab 7 breaks if a sufficiently large pressure is exerted on the surface 21, and more generally if there is exerted on the tab 7 a radial force directed inward, the force necessary for breaking the tab 7 being smaller the closer it is applied to the end surface 18.

As can be seen more particularly in FIG. 1, the surface 21 has edges parallel to the axial direction, each tab 7 having a notch 26 with an L-shaped profile between the lateral edges of the surface 21 and the lateral edges of the tab 7.

Figure 4:
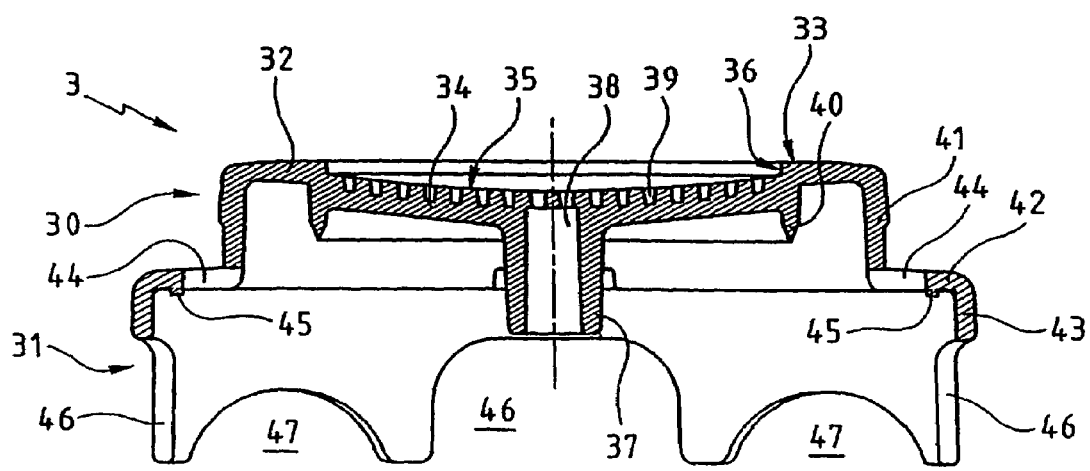

As can be seen better in FIG. 4, the drainage body 3 has a circular table 30 and a skirt 31 disposed in a step around the table 30.

The latter has an annular transverse wall 32 delimited on the opposite side from the skirt 31 by a surface 33 which is flat in the main but having a slight bevel towards the outside.

The internal periphery of the wall 32 is connected to a wall 34 delimited, on the side of the surface 33, by a surface 35 which is concave in the main, offset with respect to the surface 33 in the axial direction, towards the skirt 31, the perimeter of the surface 35 and the internal periphery of the surface 33 being connected by a slightly truncated-cone shaped surface 36.

The wall 34 is connected centrally to a pipe 37 whose internal passage is extended into the wall 34 by an output aperture 38, concentric drainage channels 39 being put into the wall 34 from the surface 35, radially oriented channels (not visible in the drawings) also being made, with the same depth as the channels 39, these radial channels opening of course into the output aperture 38, through which, therefore, there flows out all the liquid drained by the channels made in the wall 34 hollowed out with respect to the surface 35.

At the junction between the walls 32 and 34 there is situated an annular rib 40 which projects with respect to the walls 32 and 34 on the side of the skirt 31, this rib tapering towards its free end in a V-shaped profile, so that this end constitutes a sharp edge.

The table 30 also has a cylindrical lateral wall 41 which is connected by one end to the wall 32 while, by the other end, it is connected to the skirt 31.

The latter has a transversely oriented annular wall 42 and an axially oriented cylindrical wall 43, the wall 42 being connected by one of its ends to the wall 41 and by the other to the wall 43.

In the wall 42, in proximity to the wall 41, four openings 44 are made, which have between them the same angular spacing as between the latching tabs 7, that is to say they are spaced out from one another by 90°, these openings having an outline corresponding to the largest outline of the tabs 7, so that the latter can each pass through a respective opening 44.

Each opening 44 is bordered on the external side by an axially oriented tooth 45 projecting on the opposite side from the table 30.

Figure 5:
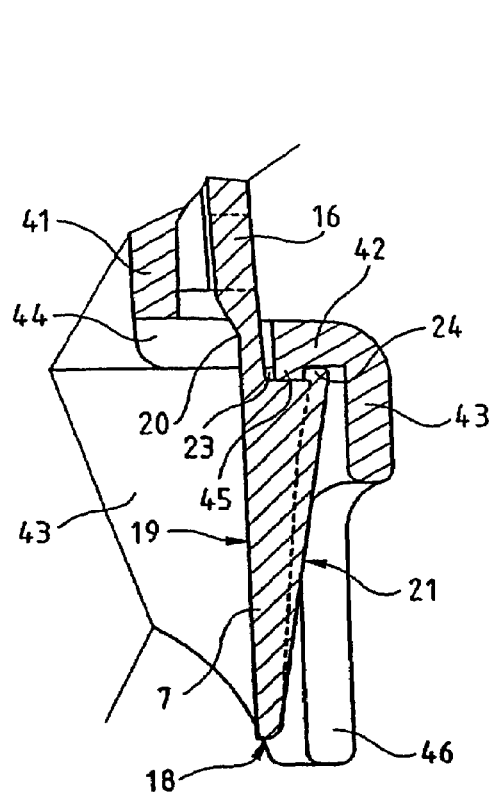
FIG. 5 is an enlargement of the part of FIG. 2 situated at the bottom right.

Each tooth 45 extends projecting over a height corresponding to the depth of the groove 23 and has a thickness less than the width of the groove 23, the distance separating each tooth 45 from the wall 43 being greater than the thickness of the shoulder 24 (see FIG. 5).

At the level of each opening 44, the wall 43 has a notch 46 of general rectangular form with rounded corners, extending over approximately two thirds of the height of the wall 43 and over a width which is approximately twice the width of the latching tabs 7.

The wall 43 also has four notches 47, each disposed halfway between two successive notches 46, the notches 47 having a rounded form whose maximum height corresponds approximately to one third of the height of the wall 43.

The drainage body 3 also has a porous pad 48 (not depicted in FIG. 4), which has a constant thickness with two opposite surfaces of the same form as the surface 35, its diameter and thickness being the same as those of the surface 36.

When the filtration body 2, the drainage body 3 and the membrane 4 are assembled, as shown notably in FIGS. 1 and 2, the membrane 4 is gripped between the edge of the lateral wall 9 of the reservoir 5 of the intake body 2 and the surface 33 of the wall 32 of the circular table 30 of the drainage body 3, the bodies 2 and 3 being locked to one another by virtue of the latching tabs 7 and the skirt 31, which are mutually disposed as can be seen more particularly in FIG. 5.

It should be noted that the tooth 45 of the wall 42 fits into the groove 23 of the tab 7 and that the shoulder 24 of this tab fits into the space situated between the wall 43 and the tooth 45, so that the cooperation between the shoulder 24 and the tooth 45 provides an extremely powerful locking of the tab 7 in the skirt 31, capable of withstanding relatively large forces tending to move the bodies 2 and 3 away from one another.

It should also be noted that the end 18 of the tab 7 is recessed with respect to the free end of the wall 43, so that, when the device 1 is put down on a surface with the drainage body 3 at the bottom, it is by means of the skirt 31 thereof that the device 1 rests on this surface, no force being exerted for this reason on the tabs 7, which therefore do not risk being broken accidentally.

Figure 3:
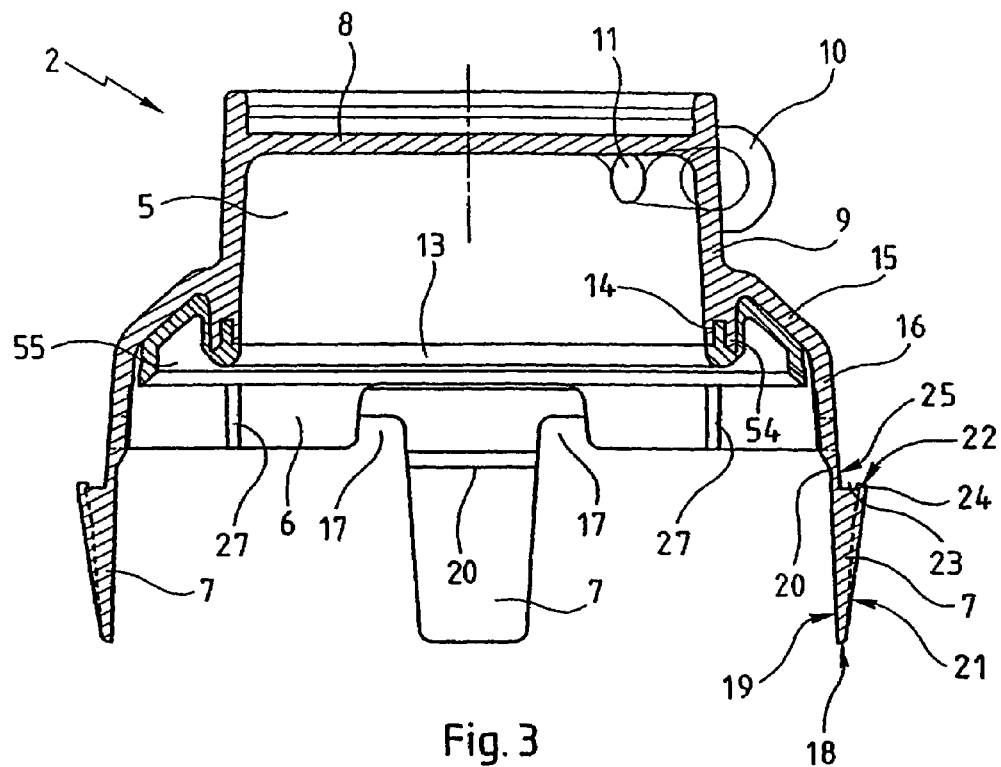
FIGS. 3 and 4 are similar views but showing, respectively, only the intake body and the drainage body.
Figure 7:
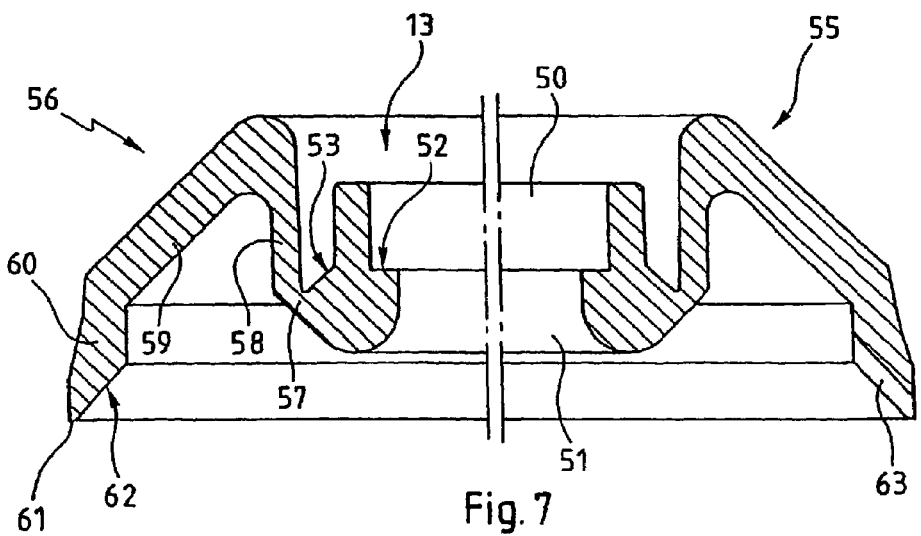
FIG. 7 is the sectional elevational view marked by VII-VII in FIG. 5, shown enlarged.

As can be seen in FIG. 2, when the device 1 is assembled, the seal 13, and more particularly the cushion thereof, is highly compressed compared with the off-load form shown in FIGS. 3 and 7.

This seal has a T-shaped general profile whose longitudinal branch forms a rib 50 designed to be inserted into the groove 14 and whose transverse branch forms a cushion 51 designed to enter into contact with the membrane 4.

It will be noted that the junction between the rib 50 and the cushion 51 is made by a straight surface 52 on the internal side while, on the external side, there is a bevel 53.

This bevel in fact corresponds to a chamfered lip 54 at the external periphery of the end of the rigid part of the wall 9, this chamfered lip making it possible to laterally contain the cushion 51 on the external side in order that it flows mainly inward, that is to say towards the chamber delimited by the membrane 4 and the reservoir 5.

In the uncompressed state, the cushion 51 has a profile whose free part, opposite to the rib 50 and to the surfaces 52 and 53, is, on the outside, rectilinear and inclined towards the outside and towards the rib 50; is, on the inside, rectilinear and oriented in the axial direction; and is, between the internal side and the external side, rounded in an arc of a circle. In the compressed state (FIG. 2), the internal side is curved whilst the part situated between the internal side and the external side, a part which is in contact with the membrane 4, is rectilinear, as is the surface 33 on which the membrane rests at this point.

It will be observed that the peripheral area of the membrane, that is to say the one which is situated radially more towards the outside than the porous pad of the support 48, is not limited to the annular portion gripped between the edge of the lateral wall 9, formed by the seal 13, and the surface 33 of the wall 32, but also has, radially further out, an annular portion disposed opposite the surface 33, extending between the portion which is gripped and the external end of the membrane 4, which is situated a little to the right of the internal surface of the wall 41.

Figure 6:
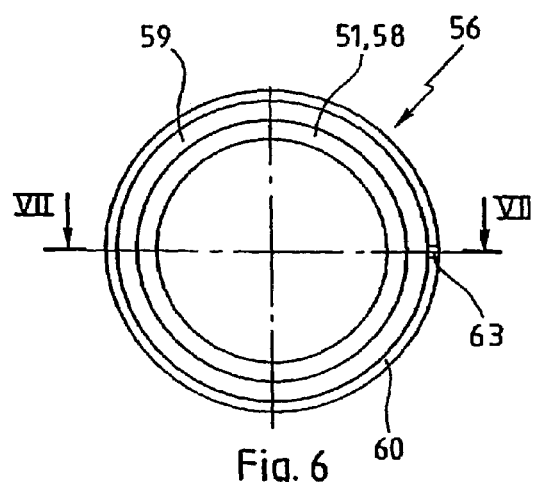
FIG. 6 is a view from below of the sealing ring with which the intake body is provided.

In order to protect this last annular portion from contamination by micro-organisms, in addition to the joint 13, a second joint 55 is provided, which has an arched profile, the external annular end of which bears against the surface 33 radially beyond the membrane 4, and whose internal annular end is connected to the seal 13, by the annular periphery thereof, the seals 13 and 55 forming together the sealing ring 56 shown in detail in FIGS. 6 and 7.

The seal 55 has, from the internal annular end 57, a cylindrical wall 58 whose internal diameter corresponds to the external diameter of the rigid portion of the wall 9 situated between the seal 13 and the skirt 6. At its end opposite to the end 57, the cylindrical wall 58 is connected, by a rounded part, to the small-diameter end of a frustoconical wall 59 whose external surface has a conformation similar to the internal surface of the frustoconical wall 15 of the skirt 6, with the small diameter of the external surface of the wall 59 corresponding to the small diameter of the internal surface of the wall 15, the large diameter of the external surface of the wall 59 on the other hand being slightly smaller than that of the internal surface of the wall 15.

The wall 59 is connected, at its end opposite to that which is connected to the wall 58, to a roughly cylindrical wall 60 which forms, opposite to its connection with the wall 59, the external peripheral end 61 of the seal 55.

The wall 60 has, on the inside, as from the end 61, a bevel 62.

It will be observed that the end by means of which the wall 60 is connected to the wall 59 is situated approximately at the same level as the external periphery of the bevel 53 and that the internal edge of the bevel 62 is situated approximately at the same level as the limit of the cushion 51 opposite to the rib 50.

Because of the dimensional characteristics which have just been disclosed, and as can be seen in FIG. 2, when the device 1 is in the assembled state, the walls 58 and 59 of the joint 55 are respectively in abutment against the external surface of the wall 9 and against the internal surface of the wall 15, whilst the portion 60 is compressed between the wall 32 and the wall 59 which is in abutment against the wall 15.

By virtue of its conformation, and in particular by virtue of the presence of the bevel 62, the wall 60 behaves like a lip which is crushed against the surface 33 of the wall 32.

A slot 63, with approximately constant and identical depth and width, is provided from the bevel 62 over the entire thickness of the wall 60. As explained below, this slot then serves for the sterilisation of the device 1, as a channel for the sterilisation agent.

Figure 8:
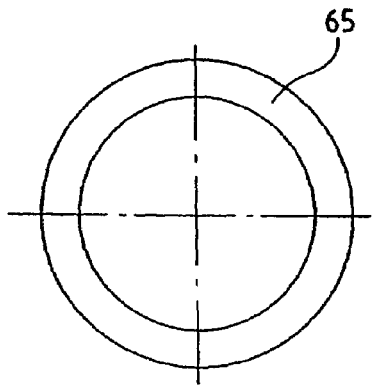
FIG. 8 is a plan view of the screen ring interposed, in the embodiment illustrated, between the membrane and the sealing ring, shown to the same scale as the latter in FIG. 6.

The screen ring 65, illustrated only in FIG. 8, is formed from a very thin film of polypropylene. Its internal diameter corresponds to the internal diameter of the edge of the lateral wall 9 of the reservoir 5, that is to say to the internal diameter of the cushion 51 when the seal 13 is not compressed, whilst the external diameter of the ring 65 corresponds to the internal diameter of the part of the wall 60 situated between the bevel 62 and the connection to the wall 59.

It is by means of the ring 65 that the joint 13 comes into contact with the membrane 4, the ring 65 being interposed between the membrane and this joint. The screen which constitutes the ring 65, because it is made from polypropylene, prevents the migration to the membrane 4 of the constituents of the elastomer material from which the sealing ring 57 is made, these constituents being liable to impair the correct growth of the micro-organisms on the membrane 4 when the latter, subsequent to the sampling operation, is put to incubate.

In addition, the screen ring 65, still because of the material from which it is made, prevents the adhesion and/or sticking of the membrane 4 to the seal 13, which could pose difficulties of recovery, or even damage to the membrane, when the device 1 is opened and the membrane is extracted from it.

In the example illustrated, a surface treatment has been carried out on the face of the ring 65 situated on the same side as the seal 13, so that the ring 65 is held on the seal 13, which facilitates still further the operations of opening the device 1 and recovering the membrane 4.

The intake body 2 is obtained, with the exception of the seal 13, by moulding a relatively rigid and transparent plastic.

The part of the drainage body 3 depicted in FIG. 4 is also made of relatively rigid moulded plastic, here white in colour, this part being next equipped, by simple fitting, with the porous pad 48.

In order to assemble the intake body 1, the drainage body 3 and the membrane 4, the latter is put on the table 30, concentrically therewith, then the intake body 2 is positioned facing the drainage body 3 with the latching tabs 7 aligned with the openings 44, then the body 2 is pressed hard towards the body 3 so that the tabs 7 engage in the openings 44 flexing slightly by virtue of the inclined surface 21 which acts as a ramp, the force exerted allowing the surface 22 of the shoulder 24 to get over the tooth 45 at the end of the pushing in movement, by virtue of the spring of the tabs 7, the seal 13 next relaxing slightly so that the play between the tabs 7 and the skirt 31 is completely taken up, the elasticity of the seal 13, which is then compressed, maintaining the locking thus obtained.

It should be noted that the maintaining of the seal in the compressed state allows it to offer excellent sealing between the membrane 4 and the edge of the wall 9, and furthermore, by reaction, between the membrane 4 and the surface 33.

The portion of the membrane 4 situated around the seal 13 is isolated from the outside by virtue of the seal 55. The arched profile of the latter and the ability of the wall 60 to deform, notably during the assembly of the bodies 2 and 3, makes it possible to create a chamber 64 opposite this portion, this chamber protecting this portion of the membrane vis-à-vis contamination by micro-organisms, and notably bacteria, coming from the environment.

In addition, the chamber 64 can collect, during an operation of sampling a liquid under pressure, any discharge from this liquid due to any lateral capillary attraction of the membrane which may remain in spite of the gripping at the seal 13.

Where the sampling relates to a particularly high volume of liquid and/or is effected over a particularly long period, so that the chamber 64 is entirely filled with liquid, the wall 60 which, as indicated above, forms a lip, deforms so that the excess liquid is discharged out of the chamber 64 and then the wall 60 resumes its place, which reconstitutes the protection vis-à-vis the outside: the wall 60 behaves like a kind of overflow valve.

It should be noted that the internal surface of the wall 16 has localized areas of extra thickness 27 (FIG. 3) coming into contact with the external surface of the wall 41, which provides a lateral wedging between these surfaces, which are of similar diameter, and more generally between the bodies 2 and 3.

It should also be noted that, once the device 1 has been assembled in this way, it is possible to package it and sterilize it with a gas such as ETO or by irradiation. By virtue of the slot 63, during sterilisation by gas, the latter enters the chamber 64, which is therefore also sterilised.

Of course, before packaging the assembled device 1 and sterilizing it, each of the pipes 10 and 37 is equipped with a stopper.

There will now be explained how the sampling of a liquid under pressure is carried out with the device 1.

First of all the stopper blocking off one of the pipes 10 and the stopper blocking off the pipe 37 are removed, then the unstoppered pipe 10 is connected to a source of liquid under pressure, for example using a sampling connector having a male Luer tip, which is inserted into the passage of the unstoppered pipe 10 and the valve of the connector is manipulated, so that the chamber formed by the reservoir 5 and the membrane 4 is raised to the same pressure as the liquid, for example 3 bars, the liquid entering the reservoir 5 through the aperture 11 and leaving the reservoir by passing through the membrane 4, which comes to rest on the porous pad 48, the liquid which has passed through the membrane 4 being guided by the channels 39 to the aperture 38, the liquid leaving the device 1 by the pipe 37, a graduated container being preferably disposed under the device 1 in order to recover the liquid coming out of the pipe 37 in order to know when the volume required for the sample has passed through the membrane 4.

When this volume has been reached, the valve on the connector is closed and the device 1 is removed from the latter, then there is put in place, in the unstoppered pipe 10, an air sterilization filter 63 (not depicted), and the drainage of the liquid still present notably in the reservoir 5 is next carried out, by suction through the output aperture 38.

It is for example possible to effect the drainage with a syringe or pump having a connector provided with a suction tip which is inserted in the passage of the pipe 37, the liquid sucked out by the tip being expelled from the syringe or pump when it is manipulated.

It will be noted that the notches 47 provided in the wall 43 make it possible to position the pump or syringe correctly vis-à-vis the device 1, according to four positions at 90° from each other.

Another possibility for extracting the liquid remaining in the device 1 after sampling is to use a vacuum phial.

Once the liquid which has remained in the device 1 has been discharged from it, the device 1 can be opened, which is done by breaking the four snapping-on lugs 7, simply by pressing on the latter through the respective notches 46, as explained above.

Another way of opening the device 1 is to release the bodies 2 and 3 by acting on the lugs 7 as indicated above, but ceasing pressing on them as soon as they are released from the tooth 45, without going as far as rupture, each of the lugs 7 being extracted out of the body 3 through the corresponding aperture 44.

It is then possible to remove the intake body 2 from the drainage body 3 and to take the membrane 4, for example with sterile tweezers, and then to place the membrane through which the sample to be examined has passed in a Petri dish, and then in a conventional manner to incubate the membrane-Petri dish assembly.

Another possibility, rather than culturing the micro-organisms outside the device 1, is to inject liquid culture medium therein using one of the pipes 10, then to drain the excess culture medium using the pipe 37, and to next put the device 1 to incubate directly, the membrane 4 being recovered only in order to identify and count the micro-organisms after incubation.

In such a case, there is an advantage in using a liquid culture medium which is slightly more concentrated than the conventional media since there always remains, notably in the pad 48, a certain amount of the sampled liquid which mixes with the injected culture medium which is therefore diluted.

In variants, not depicted, the screen ring 65 is connected to the membrane 4, for example by thermal welding, rather than to the seal 13, or then the ring 65 is connected neither to the seal 13 nor to the membrane 4; the screen ring 65 is replaced by a coating and a saturation of the peripheral area of the membrane 4 situated radially further towards the outside than the pad 48; the male and female latching elements between the bodies 2 and 3 are provided respectively on the drainage body 3 and the intake body 2, rather than the reverse; and/or use is made of latching means of different type, locking means having hinge means between the bodies 2 and 3 as well as latching means opposite the hinge means, or means of locking other than by latching.

Many other variants are possible depending on circumstances, and it should be stated in this respect that the invention is not limited to the examples described and depicted.

The invention claimed is:

1. Device for microbiological examination of a sample of liquid under pressure, having an intake body (2), a filtering membrane (4) and a drainage body (3), said intake body (2) having a reservoir (5), in one wall (9) of which a liquid input aperture (11) is made, said membrane (4) closing said reservoir (5), said drainage body (3) having means (48) of supporting said membrane (4) on the opposite side from said reservoir (5) and a liquid output aperture (38), said intake body (2) and said drainage body (3) having mutual locking means (7, 31), said membrane (4) being gripped annularly at the periphery between an annular transverse wall (32) of the drainage body (3) situated around said support means (48) of the membrane (4) and the lateral wall (9) of said reservoir (5) of the intake body (2), which lateral wall (9) has first seal (13) which forms the edge thereof and by means of which this wall (9) comes into contact with said membrane (4); wherein said intake body has a frustoconical wall connected to said lateral wall, said frustoconical wall being inclined, and wherein said device (1) is provided with a second seal (55) which has an arched profile and a frustoconical wall having an external surface having the same inclination as said frustoconical wall of said intake body, the external annular end (61) of said second seal bears against said annular transverse wall (32) radially beyond said membrane (4), and the internal annular end (57) of which is connected to said seal (13) which the lateral wall (9) of said reservoir (5) has.

2. Device according to claim 1, wherein said second seal (55) has:
   a first cylindrical wall (58) having first and second ends, said first end of which forms said internal end (57) connected to said first seal (13) and the internal surface of which is opposite a rigid part of said lateral wall (9) of said reservoir (5);
   said frustoconical wall (59) has an internal end connected to said second end of the first cylindrical wall (58); and
   a second cylindrical wall (60) having first and second ends, said first end of which is connected to said frustoconical wall (59) and said second end of which forms said external annular end (61) of said second seal (55).

3. Device according to claim 2, wherein said frustoconical wall (15) has a small-diameter end connected to said lateral wall (9) of the reservoir (5), and has a large-diameter end; and in that the internal surface of the first cylindrical wall (58) of the second seal (55) has the same conformation as the external surface of said lateral wall (9) between said first seal (13) and said frustoconical wall (15) of the intake body (2).

4. Device according to claim 3, wherein said frustoconical wall of said intake body has a small diameter end and a large diameter end, and wherein said small diameter end of said frustoconical wall (59) of the second seal (55) corresponds to the small diameter end of said frustoconical wall (15) of the intake body (2) whilst the large diameter end of said frustoconical wall (59) of the second seal (55) is slightly smaller than said large diameter end of said frustoconical wall (15) of the intake body (2).

5. Device according to either one of claims 3 or 4, wherein said frustoconical wall (15) of the intake body (2) forms part of a skirt (6) carrying said locking means (7) with which the intake body (2) is provided.

6. Device according to any one of claims 2 to 4, wherein said second cylindrical wall (60) has, on the internal side, from said external annular end (61), a bevel (62).

7. Device according to claim 6, wherein said second end of the second cylindrical wall (60) of the second seal (55) is substantially at the same level as said internal annular end (57) of said second seal (55).

8. Device according to claim 1, wherein a groove (14) is provided at the end of a rigid part of said lateral wall (9) whilst said first seal (13) has a T-shaped profile whose longitudinal leg forms a rib (50) inserted in said groove (14) and whose transverse leg forms a cushion (51) which is in contact with the membrane (4).

9. Device according to claim 8, wherein a bevel exists between the rib (50) and the cushion (51) on the external side, whilst on the internal side the rib (50) and the cushion (51) are connected by a straight surface (52).

10. Device according to claim 1, wherein said first seal (13) and said second seal (55) are formed by a sealing ring (56) moulded in a single piece.

11. Device according to claim 1, wherein it is by means of a screen ring (65) that said first seal (13) comes into contact with said membrane (4).

12. Device according to claim 11, wherein said screen ring (65) is made from polypropylene.

13. Device according to claim 12, wherein said screen ring (65) is held on said first seal (13).

14. Device according to any one of claims 11 to 13, wherein the internal diameter of said screen ring (65) corresponds to the internal diameter of a cushion (51) which said first seal (13) has.

15. Device according to any one of claims 11 to 13, wherein the external diameter of said screen ring (65) corresponds to the internal diameter of a cylindrical wall (60) situated on the external side of said second seal (55).

* * * * *